(12) United States Patent
Bakshi

(10) Patent No.: US 7,652,187 B2
(45) Date of Patent: Jan. 26, 2010

(54) SULFURIC ACID ALKYLATION PROCESS

(76) Inventor: Amarjit S. Bakshi, 20130 Chateau Bend Dr., Katy, TX (US) 77450

( * ) Notice: Subject to any disclaimer, the term of this patent is extended or adjusted under 35 U.S.C. 154(b) by 0 days.

(21) Appl. No.: 12/378,960

(22) Filed: Feb. 23, 2009

(65) Prior Publication Data
US 2009/0163758 A1 Jun. 25, 2009

Related U.S. Application Data

(63) Continuation of application No. 11/400,845, filed on Apr. 10, 2006, now abandoned.

(51) Int. Cl.
*C07C 2/62* (2006.01)
(52) U.S. Cl. .................. 585/730; 585/731; 585/718; 585/720
(58) Field of Classification Search ................. 585/730, 585/731, 718, 720
See application file for complete search history.

(56) References Cited

U.S. PATENT DOCUMENTS 5,220,094 A * 6/1993 Eason ..................... 585/716

* cited by examiner

*Primary Examiner*—Thuan Dinh Dang
(74) *Attorney, Agent, or Firm*—Richard L. Maseley

(57) ABSTRACT

A process for the sulfuric acid catalyzed alkylation of C3-C5 olefins with isobutane is disclosed wherein the requisite mixing is accomplished by the use of eductors within the reactor. In addition the alkylate product is subjected to primary and secondary coalescers for removal of entrained sulfuric acid. The vaporized unreacted C4's are recovered as liquid by absorption and desorption in an absorber oil.

5 Claims, 6 Drawing Sheets

Novel Mixing Device Reactor details
HT-Alky: $H_2SO_4$ Alkylation Process

Novel Mixing Device Reactor details
HT-Alky: H₂SO₄ Alkylation Process

HT-Alky: Acid/HC Separation

HT-Alky: BLOCK FLOW DIAGRAM

HT-Alkylation Novel C4 Vapor Recovery System

Option 1

Option 2**

Note 1: Alternate option to use Isobutane from de-isobutanizer column overhead.

SULFURIC ACID ALKYLATION PROCESS

This application is a continuation of application Ser. No. 11/400,845, which was filed on Apr. 10, 2006 now abandoned.

BACKGROUND OF THE INVENTION

1. Field of the Invention

This invention relates to a reactor/mixer design and process for an alkylation process wherein $C_3$, $C_4$ and $C_5$ olefins are reacted with isobutane to produce alkylate in the presence of sulfuric acid catalyst. In one embodiment the invention more particularly relates to a process and apparatus wherein an eductor is used in lieu of mechanical mixer to mix the sulfuric acid and hydrocarbons. In another embodiment more particularly the invention relates to a process wherein new the $C_3/C_4$ vapors from the auto refrigeration may be used in lieu of refrigeration compression. Finally in a third embodiment successive coalescing devices are used to remove the acid from the hydrocarbon to ppm level.

2. Related Information

The conventional sulfuric acid catalyzed alkylation process has been practiced in the past using mechanical propeller mixers which require complex seals. The internal mixer and seals are subjected to a hostile environment (strong sulfuric acid which is used as catalyst for the process) which is demanding. To provide the mixing and tight emulsion required for the process considerable energy is necessary for each contactor/reactor. The impellers/seals used require considerable maintenance. To facilitate the mixing conventional processes are carried out at temperatures so as to keep the viscosity low, and these temperatures are not optimum temperatures to make high octane product with low acid consumption. The operating expense of the conventional process together with complicated mixing device which has been known to require higher maintenance can be reduced.

The alkylate product in the refinery economics of gasoline, normally has very good return on investment based on the conventional process, but still the units require high investment, maintenance and liquid waste disposal. The hydrofluoric acid (HF) alkylation does not require refrigeration and acid regeneration so it is marginally better in that respect, but due to the high corrosive nature of the HF acid, exotic materials of construction are required. The process is also much more hazardous due to the HF acid, and is not readily acceptable environmentally.

Mixing devices for mixing the hydrocarbons and acids have been variously disclosed in U.S. Pat. Nos. 5,443,799; 3,696,168; 3,133,128; 4,000,212; 3,758,613 and 5,220,094. All of these patents disclose mixing devices with spray nozzles/spargers/venturi which are all low efficiency mixing equipment options and in most cases have been applied to HF Alkylation which have better reaction kinetics than sulfuric acid alkylation. The art listed in the above referenced patents does not meet the hydrodynamic requirements of an eductor with divergent portion after the nozzle. The previous art is a mixture of spray nozzles/spargers and venturi devices that produce mild mixing and are not suitable for sulfuric acid alkylation high efficiency mixing requirements. Spray nozzles and spargers do mix the liquid but they doe not provide the high efficiency as provided by an eductor. As noted, most of these earlier patents have been for HF Alkylation, though some are broad in sense but as these are do not provide the same efficiency and hydrodynamics, they cannot be accept as equivalent to eductors due to major hydrodynamics differences.

The vapor from this flash drum can be sent to an absorption column or to a compressor intermediate stage, or if the flash is done at higher pressure it can be condensed separately and recycled to the reactor with olefin feed and isobutane Due to the side reactions taking place in the process due to the impurities, acid soluble oils (ASO) which are conjunct polymers, are produced which reduce the acid concentration and fresh acid make up is needed to overcome this loss. The acid soluble oil is sent to the acid regeneration unit. The cost of acid regeneration for low acid consumption unit is about 20% of the operating cost of the alkylation unit.

SUMMARY OF THE INVENTION

An improvement in the process is herein suggested which provides an eductor in lieu of the mechanical mixers. The major improvements disclosed in the present invention are (1) the use of a mixing eductor device, (2) vapor absorption and (3) acid/hydrocarbon separation by coalescers. Additionally a new method of recovering the $C_3/C_4$ vapors from the auto refrigeration is utilized introduced for instant process. This saves capital cost by eliminating the need for a refrigeration compressor since absorption and desorption equipment is less costly than compressors.

The present invention is particularly useful in converting existing HF alkylation units to sulfuric acid alkylation units since with the present invention absorption can be used instead of adding expensive compression refrigeration equipment.

A coalescing system is provided to obtain lower than 1 ppm level of sulfur in hydrocarbon product by changing flow regimes, improving the design of coalescers and also operating the coalescing under better conditions i.e. higher temperatures than previously used.

The acid free hydrocarbon is sent to conventional alkylate recovery section after heat integration. The heat integration system, which constitutes a part of one embodiment of the present invention, where hydrocarbons are heated to flash of $C_4$'s hydrocarbon from alkylate between the coalescing stages, so that one can get better coalescing at higher temperature before the second or successive stages of coalescing and separation. The location of this flash drum provides an efficient acid separation at slightly elevated temperature of 40 to 300 F and heat integration so as to reduce the quantity of absorption or load on the compressor, if used.

The vapor from this flash drum may be sent to or to compressor intermediate stage, or if the flash is done at higher pressure it can be condensed separately and recycled to the reactor with olefin feed and isobutane recycle after cooling with the cold alkylate. The vapor from this flash drum can be sent absorption or to compressor intermediate stage or if the flash is done at higher pressure than can be condensed separately and recycled to the reactor with olefin feed and isobutane recycle after cooling with the cold alkylate. Alkylate is one of most desirable gasoline component as it is free of sulfur, aromatics and olefins. Refiners are always looking at improving this alkylation process so as to reduce the acid consumption and utilities together with maintenance costs.

The present invention operates at lower temperature which reduces the acid consumption by 40%, reducing the cost of acid regeneration. Apart from the lower acid consumption, major cost benefits of process, being unique low cost efficient mixing device, auto refrigeration vapor absorption system and enhanced acid/hydrocarbon separation equipment, which reduces the capital and operating cost of the unit.

DETAILED DESCRIPTION OF THE PREFERRED EMBODIMENT

As disclosed herein there is described a process wherein $C_3$, $C_4$ and $C_5$ mixed olefins and isobutane stream are mixed vigorously in the presence of Sulfuric acid catalyst with novel eductor) device. Internal acid piping is provided to the ejector for the motive fluid. The alkylate, which is produced at a low temperature has a better quality than the conventional process. Essentially the process works under similar acid concentration as conventional process, e.g., in the range 89 to 95% but preferably around 90 to 92% to provide the best quality product and low acid consumption, but at lower temperature than conventional process at about 20 to 50 F but preferably at 25 to 27 F essentially under isothermal conditions. The low temperature is obtained by auto refrigeration by flashing the $C_4$ hydrocarbons. Acid to olefin molar ratio is kept around 45 to 180, preferably in the range of 45 to 60, to provide the desired alkylate reaction and quality. An isobutane to olefin molar ratio of 6 to 15 is desired. These ratio's are very important and are controlled to provide the optimum conditions to lower operating expense. To provide the good mixing all the hydrocarbon streams are collected and are sent to the eductor where the acid, acting as the motive fluid, mixes all the streams with acid catalyst and reactants to provide good selectivity, and to minimize undesirable reactions.

Figure 1:
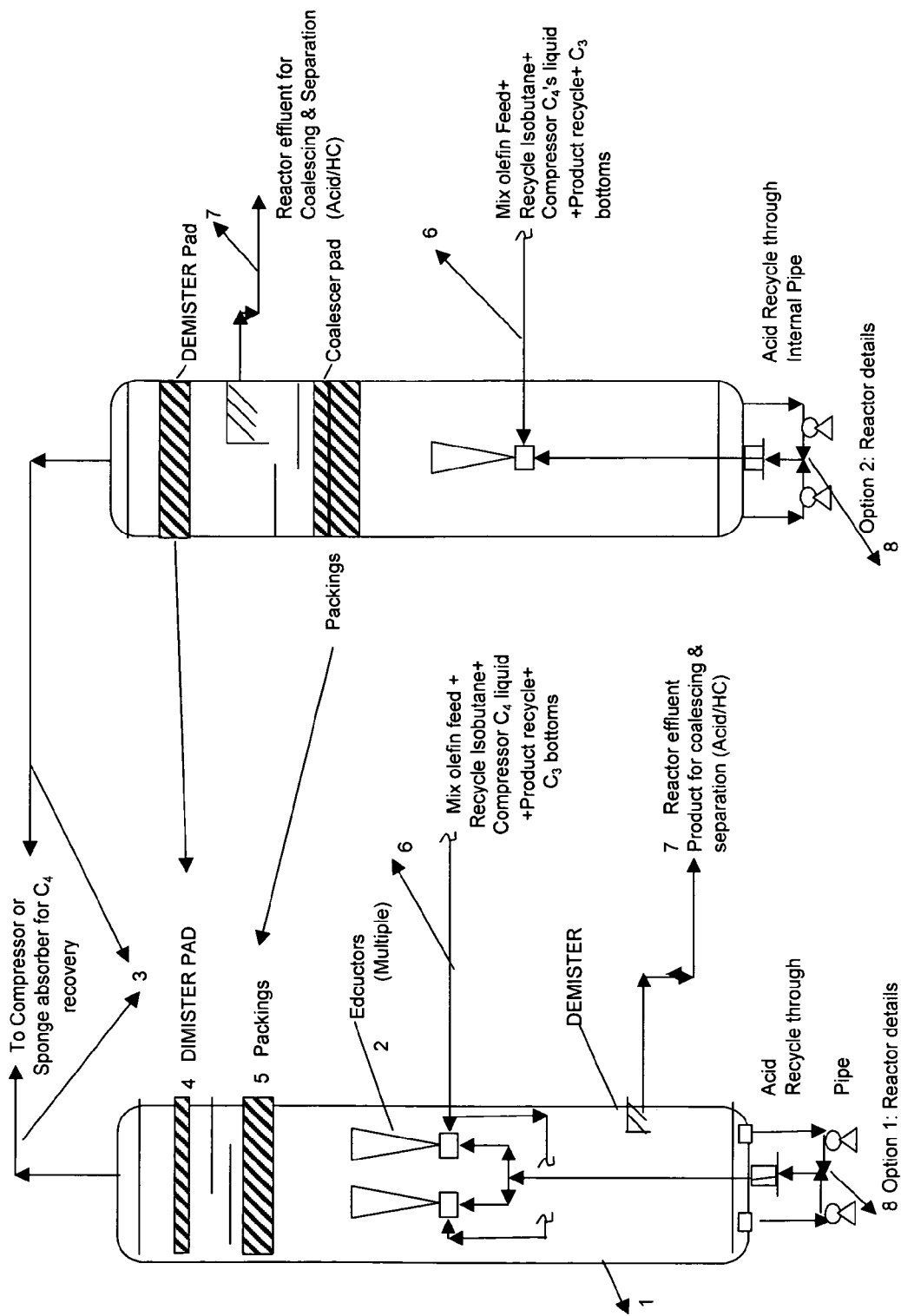
FIG. 1 is a simplified diagram of a reactor according to two separate embodiments of the invention.
Figure 2:
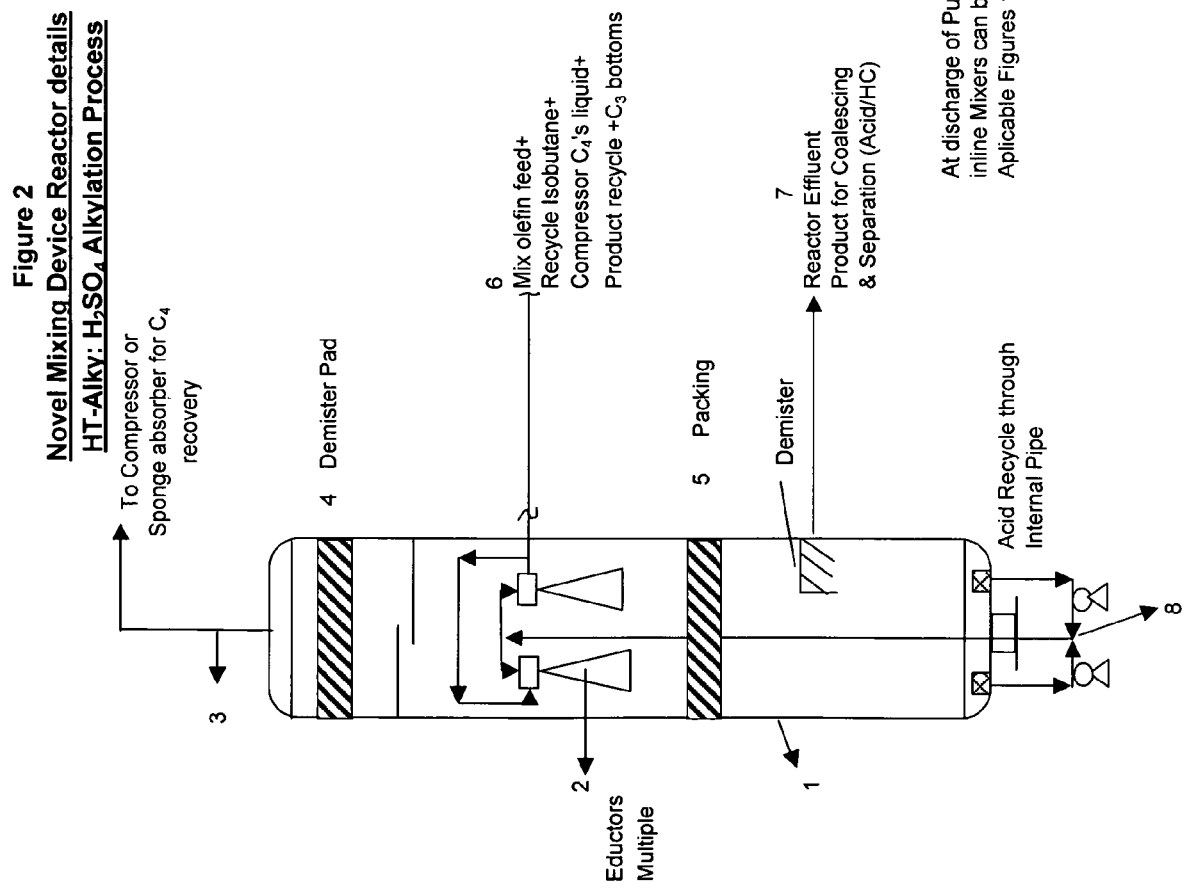
FIG. 2 is a more detailed diagram of a reactor according to one embodiment of the invention.

The disclosed methods and apparatuses can be understood by referring to the attached figures, which are described in detail herein. It should be understood that the pipelines are being designated when streams are being identified and that streams are intended, if not stated, when materials are mentioned. Moreover, flow control valves, temperature/pressure regulating devices, pumps, compressors, exchangers, drums and the like are understood as installed and operating in conventional relationships to the major equipment items which are shown in the Figures and discussed hereinafter with reference to the process of the this invention. All of these valves, devices, pumps, compressor and exchangers and the like, are included in the term auxiliary equipment. It is within the ability of one of the ordinary skill in the art to implement such auxiliary equipment, as needed in view of the present disclosure FIGS. 1 and 2 disclose an embodiment which is part of the reactor and eductor system in the process. The reactor 1 and eductor 2 are the main part of this system. The acid settles in the bottom of reactor, which is recycled by the pump back through line 8, where as the Olefin mixed stream (which includes all the C4 streams recovered and the olefin feed) is fed through line 6 to eductor to provide vigorous mixing of the acid and hydrocarbon. Packing such as intalox, saddles/raschig rings or similar, and demister pads, are provided above the eductor, in settling zone are to separate the hydrocarbon from acid with coalescing and reducing the velocity through packing. As the reactor operates in the range of 1 to 10 psig there is auto refrigeration due to evaporation of $C_3/C_4$ and some $C_5$ hydrocarbons, which are taken out by the line 3 from the Top. The reaction products together with some entrained acid and other components are taken for processing to other equipment by line 7 as shown in the FIG. 1.

In this embodiment of the invention, the eductor provides adequate and high efficiency mixing so as to have the reaction completed as it comes out of the eductor's divergent section. The vapor is generated due to auto refrigeration, and heat of reaction, which is taken as vapor stream from the top of the reactor. The reactor effluent reaction products have 20-45% alkylate, rest being isobutene/n-butane that is taken as a side draw with entrained acid which is separated down stream. As noted above, the reactor is operated at about 1 to 10 psig pressure and 25 to 27 F temperature.

Figure 3:
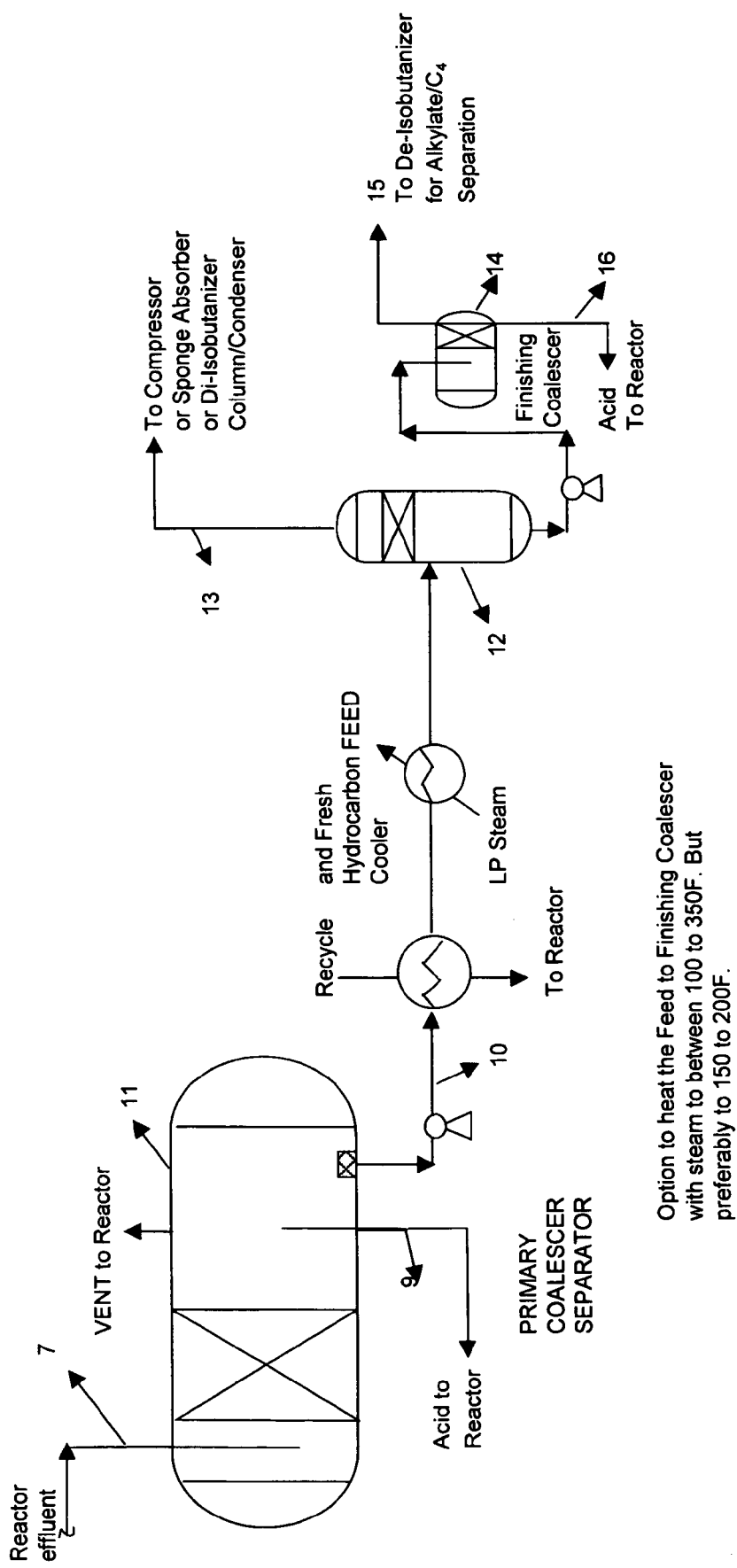
FIG. 3 is a flow diagram of the acid/hydrocarbon separation process included in the subject invention.

FIG. 3 illustrates the treatment of stream 7, which is the reactor effluent and contains alkylate, $C_4$ hydrocarbons and entrained acid. The alkylate and $C_4$ hydrocarbons are separated from the acid utilizing the multiple coalescers 11 and 14. These coalescers may be the York type or equivalent to meet the product separation requirements. The finishing coalescer can be kept at the optimum temperature to have better separation of acid and hydrocarbon in the range of 80 to 300 F. Recovered acid through line 9 is recycled to the Reactor item 1 after separation in first coalescer 11. Line 10 takes the raw mix alkylate product through heat exchangers and is flashed to remove some of $C_4$'s in flash drum 12 with the $C_4$ stream is taken for recovery via line 13. The bottoms from the flash drum 12 is sent to finishing coalescer 14 where all the residual acid is removed. The recovered acid is recycled to the reactor 1 while the raw mix alkylate stream is sent to conventional recovery system where alkylate is separated from Isobutane and n-butane.

Figure 4:
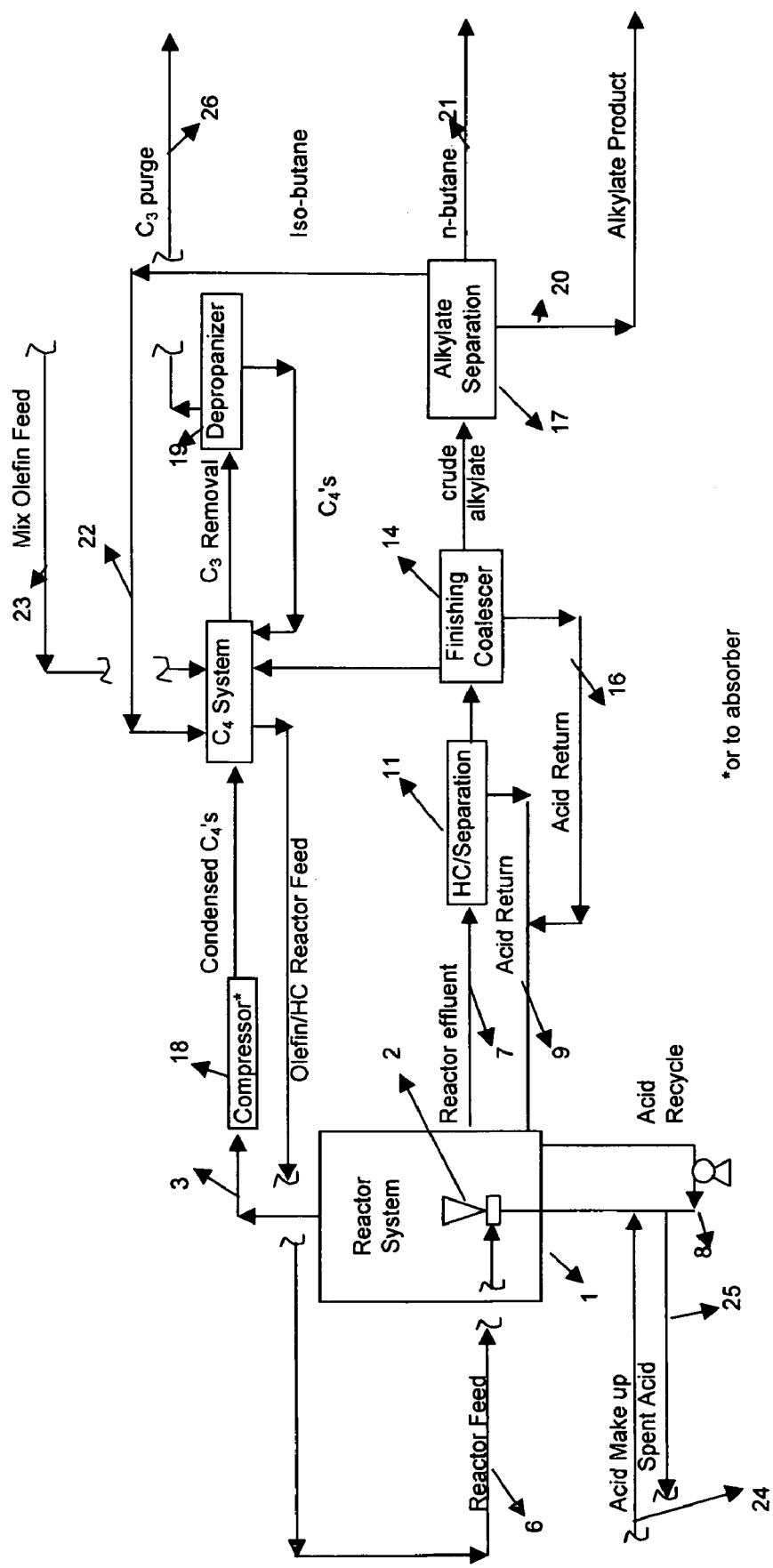
FIG. 4 is a block flow diagram of a sulfuric acid alkylation process utilizing one embodiment of the invention.

FIG. 4 provides a block flow diagram of the whole process. Acid strength is kept at about 90 to 92% by adding acid make up through line 24. In the process some adjunct polymers (ASO) are formed, which are taken out through the line 25 for acid regeneration. As shown $C_4$ vapor from line 3 is sent to existing compressor in revamp or the new absorption system of the present invention. Mixed olefin feed is mixed with all the other $C_4$ streams from the unit before sending it to the reactor. The reactor effluent from coalescer 14 is sent for alkylate recovery through line 20. The normal butane is separated and sent to offsite via line 21, while isobutane is recycled through line 22 to the reactor. Part of the $C_4$ auto refrigeration vapor after recovery is sent for lights/propane removal in depropanizer 19, and is sent off site via line 26.

This embodiment uses reactor effluent cold energy to condense the de-isobutanizer overhead and, or compressor discharge, after cooling the total hydrocarbon stream is recycled back to the reactor. This art has already been described in the U.S. Pat. No. 4,130,593 of 1978.

Figure 5:
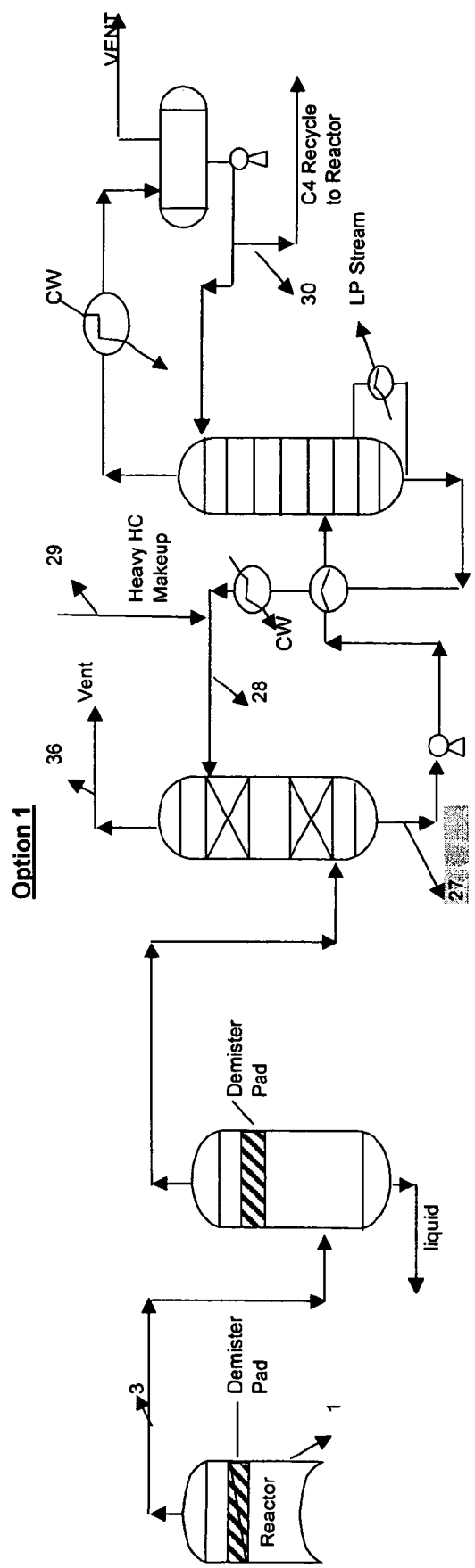
FIG. 5 is a flow diagram of one option for the $C_4$ vapor recovery in the present invention.
Figure 6:
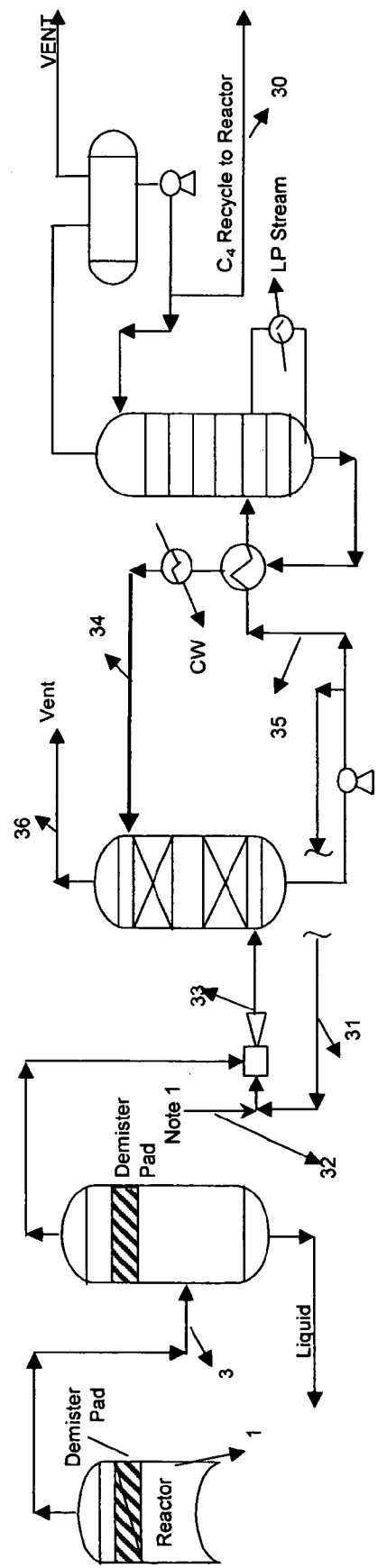
FIG. 6 is a flow diagram of a second option for the $C_4$ vapor recovery in the present invention.

The embodiment shown in FIGS. 5 and 6 teaches the absorption of $C_4$'s produced from the auto refrigeration in the reactor and taken from the reactor via line 3 in heavy naphtha, special solvent or alkylate product. In this embodiment the $C_4$ streams pressure is increased to 15 psig or higher through line 33 by using ejector where the isobutane in line 32 acts as the motive fluids for the absorption liquid in line 31 so as to make the absorption possible. In the next column, through line 35 the absorbed liquid stream is sent for recovery. The $C_4$'s are recovered through line 30 from the heavy naphtha/solvent or alkylate (whichever is used for absorption of $C_4$ vapors) and the $C_4$ stream is recycled back to the reactor. The vent through line 36 is used to control the absorption column. The second column can be reboiled with low pressure steam and will be a cheaper alternate to the compressor option and can also be used when revamping any unit where the compressor is a bottleneck. Likewise it may be used for the conversion of HF units to sulfuric acid units.

The back end of the unit is a simple de-isobutanizer as one column system or two-column system to separate the isobutane and n-butane from Alkylate. The straight chain olefins provide the slightly higher octane alkylate from the sulfuric acid alkylation compared to branch chain olefins, and the acid consumption for branched chain olefins is higher as well. So straight chain olefins $C_3$, $C_4$ and $C_5$ are the preferred olefin species.

Reactions

The reaction of olefins with isobutane produces trimethyl pentanes (TMP) which are the desired reaction products. The $C_3$ olefins provide more of dimethyl pentane (DMP) in the alkylate and $C_5$ olefins provide more of $C_9$ alkylate component giving lower octane product compared to $C_4$ olefins. The straight chain olefins provide the slightly higher octane alkylate from the sulfuric acid alkylation compared to branch chain olefins, and the acid consumption for branched chain olefins is higher as well. So straight chain olefins $C_3$, $C_4$ and $C_5$ are the preferred Olefin species. In the Sulfuric Acid alkylation process, olefins and isobutane are reacted in the presence of sulfuric acid catalyst at 20 to 60 F to form essentially TMP and some other byproducts like di-methyl hexanes (DMH) and DMP are formed.

Alkylation Chemistry

Butylenes+Isobutane→TMP

Propylene+Isobutane→DMP

It should be noted that even though in $C_4$ alkylation TMP has high concentration over 60 to 70% in the alkylate product, but other components are e.g. DMH and DMP, which are formed in the alkylation reaction.

The side reactions can be postulated as follows:

Polymerization olefin+olefin→Polymer $C_6$, $C_8$ and $C_{12}$ etc

Cracking

In the reaction larger compounds are made which crack to make smaller compounds:

$C_{11}H_{24}$→$C_6H_{12}$+$C_5H_{12}$

Hydrogen Transfer Reactions

This reaction takes place by transferring hydrogen to olefin to make paraffin. Essentially Isopentane is made in the reaction.

$2C_4H_{10}+C_5H_{10}$→$C_8H_{18}+C_5H_{12}$

Esterification Reaction

Sulfuric acid reacts with olefins to form small amount of di-butyl sulfate, which is unstable at high temperature and is removed in the coalescer so as to produce good quality product.

Disproportionation

This takes place by rearrangement of the hydrocarbons to form different molecules from a larger hydrocarbon molecule.

$2C_{10}H_{22}$→$C_8H_{18}+C_{12}H_{26}$

The Relative Reaction Rates of Olefins Influence the Product Quality and Relative Conversion Rates can be Postulated as Follows:

n-butene>i-butene>isopentenes>n-pentenes>propylene

From the above one can deduce that one needs lower space velocity for pentenes and even lower for propylene compared to butylenes.

The mixing is done in the eductor and in the reactor where predominantly TMP mixture, and 20 to 35% of other DMH, DMP and heavy compounds e.g. nonanes are produced.

As it has already been illustrated by prior art U.S. Pat. No. 5,095,168 that when working at lower temperatures, around 10 to 50 F, preferably at 25 to 28 F, the selectivity to TMP is better providing better octane and also lower acid consumption. The present invention is being practiced at the most desired temperature conditions, at isothermal conditions, which provide even better results for selectivity.

EXAMPLE

| Feed, | wt % |
|---|---|
| Propane/Propylene | 0.6 |
| Isobutane | 15.5 |
| Isobutylene | 14.7 |
| 2-butene | 38.5 |
| 1-Butene | 14.6 |
| N-butane | 15.8 |
| C5's | 0.3 |
| Total | 100.0 |

The above feed is used for to produced alkylate and the simulated results are very good. The Road Octane was observed to be 94.5 to 95.0 with research octane clear to be 95.5 to 96.0 and motor octane Clear to be 93.5 to 94.0.

The invention claimed is:

1. A process for the sulfuric acid catalyzed alkylation of C3-C5 olefins with isobutane comprising the steps of:
   (a) feeding sulfuric acid to an eductor in a reactor;
   (b) feeding a hydrocarbon stream containing C3-C5 olefins and isobutane to said eductor wherein the sulfuric acid acts as the motive fluid to intimately mix the sulfuric acid with the hydrocarbon stream;
   (c) reacting a portion of the $C_3$-$C_5$ olefins with a portion of the isobutane to produce a product stream containing a hydrocarbon portion comprising alkylate product, unreacted $C_4$'s, and entrained sulfuric acid;
   (d) separating the hydrocarbon portion of the product stream from the sulfuric acid within the reactor by contact with a first demister pad;
   (e) removing the hydrocarbon stream from the reactor for further processing; and
   removing the sulfuric acid from the reactor for recycle to the feed.

2. The process according to claim 1 wherein the hydrocarbon portion is further processed in a coalescer to remove sulfuric acid.

3. The process according to claim 1 wherein the pressure of the $C_4$'s is increased by the use of an ejector and the C4's are absorbed in an absorber fluid comprising heavy naphtha.

4. A process for the sulfuric acid catalyzed alkylation of C3-C5 olefins with isobutane comprising the steps of:
   (a) feeding sulfuric acid to an eductor in a reactor;
   (b) feeding a hydrocarbon stream containing C3-C5 olefins and isobutane to said eductor wherein the sulfuric acid acts as the motive fluid to intimately mix the sulfuric acid with the hydrocarbon stream;
   (b) reacting a portion of the $C_3$-$C_5$ olefins with a portion of the isobutane to produce a product stream containing a hydrocarbon portion comprising alkylate product, unreacted $C_4$'s, and entrained sulfuric acid;
   (c) separating the hydrocarbon portion of the product stream from the sulfuric acid within the reactor by contact with a first coelescer;
   (d) subjecting hydrocarbon from step (c) to a second coelescer to remove further sulfuric acid;
   (e) separating the unreacted $C_4$'s from the alkylate product;
   (f) increasing the pressure of the unreacted C4's in an ejector and subjecting the unreacted C4's to absorption in an absorber fluid;
   (g) removing the unreacted C4's from the absorber fluid as a liquid;
   (h) returning the liquid C4's to the feed stream of step (b)
   (i) recovering the acid from the coelescers of steps (c) and (d):
   (j) returning the recovered acid from step (i) to the acid stream of step (a).

5. The process according to claim 1 wherein the pressure of the $C_4$'s is increased by the use of an ejector and the C4's are absorbed in an absorber fluid comprising alkylate.

* * * * *